(12) United States Patent
Ranade et al.

(10) Patent No.: US 10,336,681 B2
(45) Date of Patent: Jul. 2, 2019

(54) PROCESS FOR THE SYNTHESIS OF DIALKYL CARBONATES

(71) Applicant: Council of Scientific & Industrial Research, New Delhi (IN)

(72) Inventors: Vivek Vinayak Ranade, Maharashtra (IN); Ashutosh Anant Kelkar, Maharashtra (IN); Vilas Hari Rane, Maharashtra (IN); Anil Kisan Kinage, Maharashtra (IN); Savita Kiran Shingote, Maharashtra (IN); Lalita Sanjib Roy, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 15/560,821

(22) PCT Filed: Mar. 23, 2016

(86) PCT No.: PCT/IN2016/050093
§ 371 (c)(1),
(2) Date: Sep. 22, 2017

(87) PCT Pub. No.: WO2016/151602
PCT Pub. Date: Sep. 29, 2016

(65) Prior Publication Data
US 2018/0319734 A1 Nov. 8, 2018

(30) Foreign Application Priority Data
Mar. 23, 2015 (IN) .............................. 794/DEL/2015

(51) Int. Cl.
| | | |
|---|---|---|
| *C07C 68/00* | (2006.01) | |
| *B01J 37/03* | (2006.01) | |
| *B01J 23/00* | (2006.01) | |
| *B01J 23/10* | (2006.01) | |
| *B01J 23/83* | (2006.01) | |
| *B01J 35/00* | (2006.01) | |
| *B01J 35/02* | (2006.01) | |
| *B01J 35/10* | (2006.01) | |
| *B01J 23/02* | (2006.01) | |
| *B01J 37/02* | (2006.01) | |
| *B01J 37/08* | (2006.01) | |

(52) U.S. Cl.
CPC .............. *C07C 68/00* (2013.01); *B01J 23/002* (2013.01); *B01J 23/02* (2013.01); *B01J 23/10* (2013.01); *B01J 23/83* (2013.01); *B01J 35/002* (2013.01); *B01J 35/0006* (2013.01); *B01J 35/023* (2013.01); *B01J 35/1014* (2013.01); *B01J 37/0236* (2013.01); *B01J 37/031* (2013.01); *B01J 37/036* (2013.01); *B01J 37/08* (2013.01); *B01J 2523/00* (2013.01)

(58) Field of Classification Search
CPC ................................. C07C 68/00; B01J 23/02
See application file for complete search history.

(56) References Cited

U.S. PATENT DOCUMENTS

| | | | |
|---|---|---|---|
| 4,436,668 A | | 3/1984 | Harder et al. |
| 5,767,303 A | * | 6/1998 | Minami ............... B01J 31/0202 502/165 |
| 6,162,940 A | | 12/2000 | Chang et al. |
| 9,475,780 B2 | * | 10/2016 | Gupta .................. C07D 233/34 |
| 9,920,000 B2 | * | 3/2018 | Ranade .................. C07C 68/00 |
| 2006/0047136 A1 | | 3/2006 | Sun et al. |
| 2010/0312001 A1 | | 12/2010 | Wershofen et al. |
| 2014/0094621 A1 | | 4/2014 | Koh et al. |

FOREIGN PATENT DOCUMENTS

| | | |
|---|---|---|
| CN | 1416949 | 5/2003 |
| EP | 0-478073 A2 | 4/1992 |
| EP | 1629888 A1 | 3/2006 |
| EP | 2700629 A2 | 2/2014 |
| WO | WO-2009052996 A1 | 4/2009 |
| WO | WO-2011013880 A2 | 2/2011 |
| WO | WO-2015132801 A1 | 9/2015 |

OTHER PUBLICATIONS

International Search Report and Written Opinion issued in PCT/IN2016/050093 dated Sep. 20, 2016.

Shumin X. et al., "Synthesis of diethyl carbonate from urea and ethanol over lanthanum oxide as a heterogeneous basic catalyst," Fuel Processing Technology, vol. 126, Oct. 1, 2014, pp. 453.459.

Wang D. et al., "Synthesis of dimethyl carbonate from methyl carbamate and methanol catalyzed by mixed oxides from hydrotalcite-like compounds," Journal of Physics and Chemistry of Solids, Pergamon Press, London GB, vol. 71, No. 1, Apr. 1, 2000, pp. 427-430.

Wang D. et al., "Synthesis of dimethyl carbonate from methyl carbamate and methanol using a fixed-bed reactor," Chemical Engineering & Technology, vol. 35, No. 12, Dec. 6, 2012, pp. 2183-2188.

(Continued)

*Primary Examiner* — Golam M Shameem
(74) *Attorney, Agent, or Firm* — Blank Rome LLP

(57) ABSTRACT

The patent discloses a process for the synthesis of dialkyl carbonates catalyzed by a catalyst composition AB oxides, wherein A and B are rare earth metals or A and B are combination of rare earth and transition metals with ratios ranging from 0.5:10 to 10:0.5.

13 Claims, 3 Drawing Sheets

(56) References Cited

OTHER PUBLICATIONS

Wang M. et al., "High-yield synthesis of dimethyl carbonate from urea and methanol using a catalytic distillation process," Industrial & Engineering Chemistry Research, vol. 46, No. 9, Apr. 1, 2017, pp. 2683-2687.
Li F. et al., "Magnesium-oxide nanosheets as effective catalysts for the synthesis of diethyl carbonate from ethyl carbamate and ethanol," Catalysis Science & Technology, vol. 5, No. 2, Jan. 1, 2015, pp. 1021-1034.
Wang D. et al., "Zn/Fe mixed oxide: heterogeneous catalyst for the synthesis of dimethyl carbonate from methyl carbamate and methanol," Catalysis Communications, Elsevier Science, Amsterdam, NL, vol. 11, No. 5, Jan. 23, 2010, pp. 430-433.
Wang M.H. et al., "Synthesis of dimethyl carbonate from urea and methanol over solid base catalysts," Catal Commu., vol. 7, 2006, pp. 6-10.
"Effect of the Preparation Method on the Properties of Zirconia-Ceria Materials" Sylvie Rossignol et al., in J. Materials Chem., 1999, vol. 9, pp. 1615-1650.
"CEO2—ZrO2 Solid Solution Catalyst for Selective Synthesis of Dimethyl Carbonate from Methanol and Carbon Dioxide" Keiichi Tomishige in Catalysis Letters, Sep. 2001, vol. 76, Issue 1, pp. 71-74.

\* cited by examiner

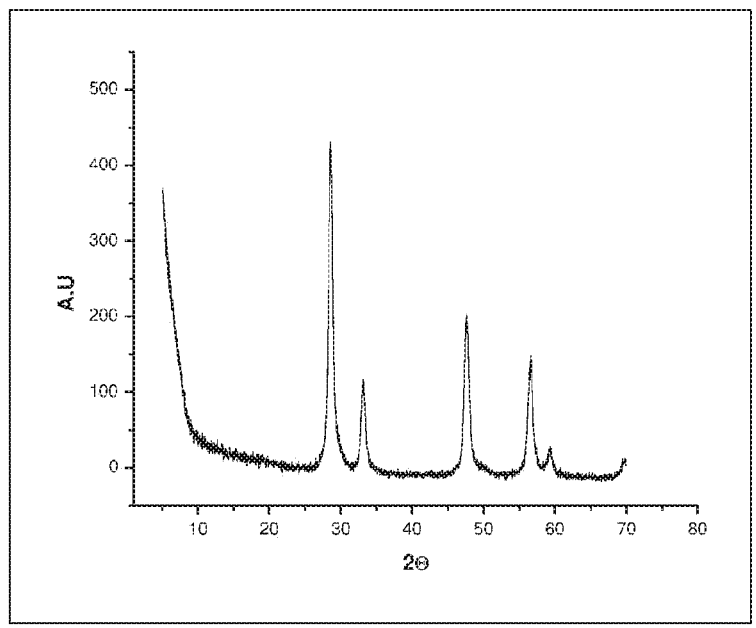
Fig: 1

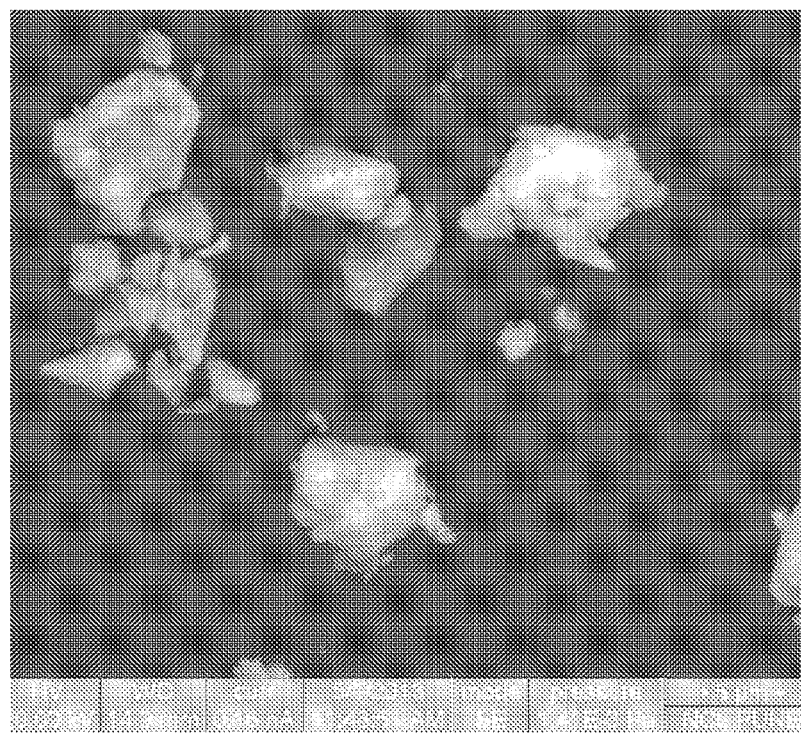
Fig: 2

PROCESS FOR THE SYNTHESIS OF DIALKYL CARBONATES

RELATED APPLICATION

This application is a national phase of PCT/IN2016/050093, filed Mar. 23, 2016, which claims benefit to Indian Patent Application No. 794/DEL/2015, filed Mar. 23, 2015. The content of these applications are hereby incorporated by reference.

FIELD OF THE INVENTION

The present invention relates to a process for the synthesis of dialkyl carbonate. Particularly, the invention relates to the synthesis of Dimethyl carbonate (DMC) and related compounds further, starting from methyl carbamate (MC) and methanol employing catalyst, wherein the catalyst is a mixed metal oxide composition of rare earth/transition metals calcined at higher temperature.

BACKGROUND AND PRIOR ART OF THE INVENTION

Dimethyl carbonate (DMC) is an important intermediate and is widely used in industry. Owing to its low toxicity, dimethyl carbonate is considered a "green" chemical product with bright development prospects. DMC is a versatile chemical and has been used mainly as a methylating and methoxy carbonylating agent as a safe substitute for dimethyl sulphate, phosgene or methyl halide, which are toxic or corrosive. It can also be used as a solvent to replace halogenated solvents. DMC has a potential application as fuel additive for gasoline to improve octane number and could lead to increase in demand of DMC. This increasing focus on the use of DMC is mainly due to the bio-degradability, with a low bioaccumulation as well as its low toxicity.

US 20140094621 A1 discloses a method for preparing dialkyl carbonate from urea or alkyl carbamate and alkyl alcohol using a metal oxide catalyst selected from the group consisting of CaO, MgO, ZnO, PbO, La2O3, Y2O3 and hydrotalcite and an ionic liquid comprising a cation, which produces a hydrogen ion, and a hydrophobic anion containing fluorine with high temperature stability.

WO 2009/052996 A1/US 20100312001 A1 A catalyst for the synthesis of an organic carbonate comprising a calcinate prepared by calcining a rare earth element containing hydrous salt at a calcining temperature within the range of 150° C. to 450° C.

Article titled, "CeO2-ZrO2 Solid Solution Catalyst for Selective Synthesis of Dimethyl Carbonate from Methanol and Carbon Dioxide" by Keiichi Tomishige in Catalysis Letters, September 2001, Volume 76, Issue 1, pp 71-74 reports $CeO_2$—$ZrO_2$ solid solution catalysts are very effective for the selective synthesis of dimethyl carbonate from methanol and $CO_2$. The activity was much dependent on the calcination temperature. The higher the calcination temperature, the higher the activity of the catalyst for DMC formation, though the BET surface area is lower on the catalyst calcined at higher temperature Article titled, "Effect of the preparation method on the properties of zirconia-coria materials" Sylvie Rossignol, François Gérard and Daniel Duprez *J. Mater. Chem.*, 1999, 9, 1615-1620 reports Zirconium-cerium mixed oxides were prepared by two Methods: (i) sol-gel hydrolysis of alcoholic solutions of zirconium alkoxides (n-propoxide and n-butoxide) in the presence of aqueous solutions of cerium nitrate (method SG) or (ii) coprecipitation of aqueous solutions of zirconyl and cerium nitrates by ammonia (method NP).

Article titled, "Synthesis of Dimethyl Carbonate from Urea and Methanol over Solid Base Catalysts" by Wang M H et al in Catal Commun, vol 7, pp 6-10, 2006 reports CaO as catalyst.

CN 1416949 A discloses synthesis of dimethyl carbonate from urea and methanol with a metal oxide catalyst, wherein: it is made of lithium, magnesium, nickel, zinc, lead, iron, aluminum, molybdenum, zirconium, lanthanum metal oxides 1-3 composition; wherein the mixed metal oxide catalyst must be zinc oxide as the main body, the percentage by weight of 35 to 95%, by weight of the other metal oxides and from 5 to 65%, when the catalyst is a mixed metal oxide in three, the other two metal oxides other than the percentage by weight of zinc oxide as 1:1.

US 20060047136 A1 discloses A catalyst for the preparation of dimethyl carbonate from urea and methanol, characterized in that the catalyst has a composition on weight base of: active component: from 20 to 50 wt % and carrier: from 80 to 50 wt %, Wherein, the carrier is selected from the group consisting of active carbon, α-alumina, γ-alumina, silica, and molecular sieve; and the active component is one or more selected from the group consisting of oxides and chlorides of alkali metals, alkali-earth metals, and transition elements.

U.S. Pat. No. 4,436,668A discloses Carbonates prepared by reacting carbamic acid esters with alcohols at above 140° C., wherein the ammonia formed is stripped from the reaction mixture during the reaction.

U.S. Pat. No. 6,162,940 A discloses a method for co-producing dialkyl carbonate and alkanediol by reacting alkylene carbonate with alkanol in the presence of a complex salt catalyst having a formula $A_x(M_y O_z)$, wherein A is an alkali metal or alkaline earth metal, M is a Group 5 or Group 6 transition metal, O is oxygen, x is 1 or 2, y is 1 or 2, and z is an integer from 3 to 6.

EP 0478073 A2 discloses a process for producing a dialkyl carbonate by contacting an alkylene carbonate with an alkanol in the presence of a mixed metal oxide catalyst or a modified bimetallic or polymetallic catalyst.

WO 2015132801 A1, WO 2014072803 A1 and WO 2014072802 A2 disclose other routes for synthesis of dimethyl carbonate and related compounds using different catalysts.

The main disadvantages of the reported routes are: the slow reaction rate of epoxides with $CO_2$ and requirement of high pressures, and the exchange reaction of the cyclic carbonate with methanol are limited by equilibrium. The economy of the processes is affected due to the use of epoxide which is expensive and formation of ethylene glycol as a by-product in stoichiometric quantity.

Therefore, it is the need to develop an efficient process for the synthesis of dialkyl carbonates.

OBJECTIVES OF THE INVENTION

The main object of the present invention is to provide an efficient process for synthesis of dialkyl carbonate.

Another object of the present invention is to provide a novel catalyst system for the synthesis of dialkyl carbonate particularly DMC and other compounds.

SUMMARY OF THE INVENTION

Accordingly, present invention provides a process for the synthesis of dialkyl carbonates catalysed by a catalyst composition AB oxides, wherein A and B are rare earth metals or A and B are mixture of rare earth and transition metals with ratios ranging from 0.5:10 to 10:0.5.

In an embodiment of the present invention, the said process for the synthesis of dialkyl carbonates comprises the steps of:
i. charging alkyl carbamate and aliphatic alcohol (1:5) in a high pressure reactor, adding the catalyst and heating the reactor to 100-300° C. with stirring; and
ii. removing ammonia formed over the period of reaction and cooling the reaction to room temperature at temperature in the range of 20 to 30° C. to obtain the desired alkyl carbonate.

In yet another embodiment of the present invention, dialkyl carbonates are selected from di methyl carbonate (DMC), di ethyl carbonate (DEC), di propyl carbonate (DPC) or di butyl carbonate (DBC).

In yet another embodiment of the present invention, the catalyst is a mixed metal oxide, said metal selected from rare earth/inner transition elements or transition metals.

In yet another embodiment of the present invention, said catalyst is optionally a ternary mixed metal oxide having more than two elements used in combination in the molar ratio a:b:c, where element "a" is in a range of 0.1 to 1; element "b" is in a range of 0.1 to 1-x and element "c" is x, wherein x is in the range of 0.01 to 0.09, wherein said elements are selected from rare earth, transition metals and alkaline earth metals.

In yet another embodiment of the present invention, the element is selected from Zr, Ce, Fe or La.

In yet another embodiment of the present invention, metal oxide is CeZrO.

In yet another embodiment of the present invention, the catalyst is supported or unsupported and the support is selected from carbon, neutral alumina or silica.

In yet another embodiment of the present invention, the process is conducted with $CO_2$ or $N_2$ stripping.

In yet another embodiment of the present invention, the process is conducted in batch or continuous mode in an autoclave, packed bed reactor, bubble column reactor or such like.

In yet another embodiment of the present invention, conversion of alkyl carbamate is >30% and selectivity is more than 30% to the corresponding alkyl carbonate.

BRIEF DESCRIPTION OF THE DRAWINGS

FIG. 1: XRD of CeZrO catalyst.
FIG. 2: SEM of CeZrO catalyst.

DETAILED DESCRIPTION OF THE INVENTION

Figure 3A:
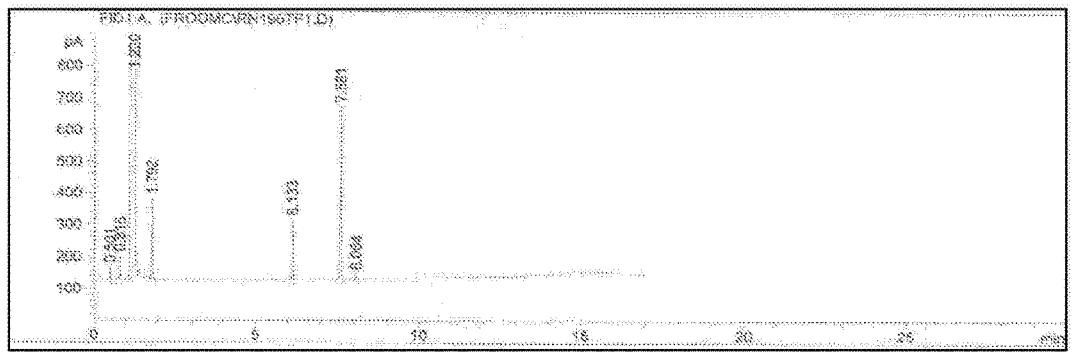
FIG. 3: 3A Gas Chromatography Chart for Di methyl carbonate (DMC) and Methyl-; N-Methyl carbamate (MNMC) formation with CeZrO
Catalyst: 3B Gas Chromatography Mass Spectroscopy (GCMS) Chart for DMC and MMC formation with CeZrO Catalyst.
Figure 3B:
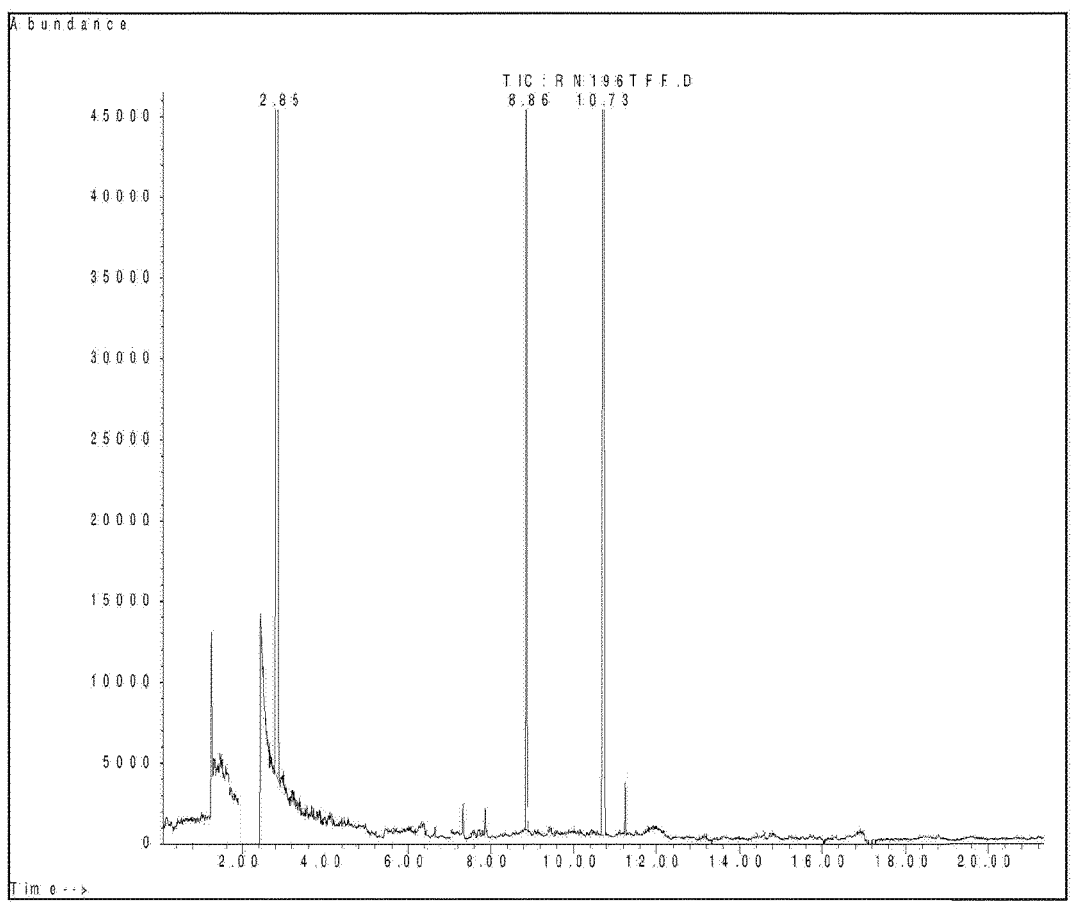

Present invention provides a process for the synthesis of dialkyl carbonate catalyzed by mixed metal oxides of rare earth metals/transition metals calcined at higher temperature.

The present invention provides a process for the synthesis of dialkyl carbonates comprising reacting methanol and methyl carbamate (MC) in presence of novel catalyst system is to obtain the desired carbonates.

The present invention provides a process wherein dialkyl carbonates are selected from di methyl carbonate (DMC), di ethyl carbonate (DEC), di propyl carbonate (DPC) or di butyl carbonate (DBC).

The present invention provides a process wherein the catalyst is a mixed metal oxide. The present invention provides a catalyst for the process wherein the Metal is selected from rare earth/inner transition elements or transition metals.

In a more preferred embodiment, the present invention provides a catalyst for the process wherein the elements are selected from, but not limited to Zr, Ce, Fe or La.

The present invention provides a catalyst for the process wherein the elements are used in combinations in the ratio 0.5:10 to 10:0.5.

In a more preferred embodiment the present invention provides a catalyst for the process wherein the ratio is 1:1 to 5:1.

The present invention provides a catalyst for the process wherein mixed metal oxide is CeZrO.

in an aspect, the invention provides a process using mixed metal oxide catalysts for the preparation of di alkyl carbonates, wherein the catalysts are prepared by employing co-precipitation and urea hydrolysis method.

In another aspect of the invention, mixed metal oxides contain combination of metal oxides synthesized from rare earth/inner transition elements or transition metals calcined at higher temperature, preferably in the range of 500° C. to 900° C. to obtain the catalyst.

In yet another aspect of the invention, the catalyst is prepared by a process comprising:
a. mixing solution A comprising of a first metal nitrate with solution B comprising of a second metal nitrate in distilled water;
b. adding the solutions A and B of step (a) drop wise to water to cause precipitation by maintaining pH between 9-10 and aging the precipitate in mother liquor under stirring;
c. filtering and washing the precipitate of step (b) with distilled water till pH 7 was obtained to get rid of alkali and $NO_3^-$ ions;
d. drying the precipitate of step (c) and crashing to a fine powder; and
e. calcining the powder of step (d) under air flow at 500° C. to 900° C. to obtain the desired catalyst.

In step (b) of the co precipitation process for the preparation of the mixed metal oxide catalyst, pH adjustment may be carried out using agent selected from NaOH, citric acid or ammonia.

In still another aspect, mixed metal oxides containing combination of metal oxides are synthesized using urea hydrolysis method from rare earth/inner transition elements or transition metals calcined at higher temperature preferably between 500° C. to 900° C. to obtain the catalyst.

In another aspect of the invention, the catalyst is prepared by a process comprising:
a. mixing solution A comprising of a first metal nitrate with solution B comprising of a second metal nitrate in distilled water and adding urea such that urea:nitrate ion ratio is 1.6:1;
b. refluxing the solution of metal nitrates and urea of step (a) for 48 h;
c. filtering and washing the solution of step (b) with distilled water and then with ethanol to remove any un-complexed nitrate ions to obtain a solid precursor as a precipitate;

d. drying the precipitate of step (c) and crushing to a fine powder; and
e. calcining the powder of step (d) under air flow to obtain the desired catalyst.

The present invention provides a process wherein the catalyst is supported.

The present invention provides a catalyst for the process wherein the support is selected from carbon, neutral alumina or silica.

The present invention provides a process wherein the catalyst is without support.

The catalyst is characterized with respect to surface area in the range of 50 to 150 m$^2$/g. The catalyst is characterized by XRD and SEM (Refer FIGS. 1 and 2).

The invention provides a process for the synthesis of dialkyl carbonates comprising the steps of:
(a) Charging alkyl carbamate and aliphatic alcohol (1:5) in a high pressure reactor, adding the catalyst and heating the reactor to 100-300° C. with stirring; and
(b) Removing ammonia formed over the period of reaction and cooling the reaction to room temperature in the range of 20 to 30° C. to obtain the desired alkyl carbonate.

The invention provides a process for the synthesis of alkyl carbonates wherein conversion of alkyl carbamate is >30%, with >30% selectivity to the corresponding alkyl carbonate.

The process of synthesis of di alkyl carbonates is conducted with CO2 or N2 stripping.

The process may be conducted in batch or continuous mode in an autoclave, packed bed reactor, bubble column reactor or such like.

EXAMPLES

Following examples are given by way of illustration and therefore should not be construed to limit the scope of the invention.

Preparation of Mixed Metal Oxides

Example 1: Zr—Ce Oxide

Hydrated ceria-zirconia oxide was obtained by co precipitation method. Cerium nitrate 0.3 mol and zirconyl nitrate 0.1 mol were dissolved in 100 ml water to prepare mixed nitrate solution. This solution was then added to 500 ml water at room temperature at 25° C. with constant stirring. This solution was maintained at pH 9 by adding 14.7 molar NH$_3$ solution (17 ml). White precipitate thus obtained was aged overnight for 12 hr, isolated by filtration, dried and calcined at 900° C. for 4 hrs.

Example 2: Zr—La Oxide

Hydrated lanthanum zirconia oxide was obtained by co precipitation method. Lanthanum nitrate 0.1 mol and zirconyl nitrate 0.3 mol were dissolved in 100 ml water to prepare mixed nitrate solution. This solution was then added to 500 ml water at room temperature at 25° C. with constant stirring. This solution was maintained at pH 9 by adding 14.7 molar NH$_3$ solution (17 ml). White precipitate thus obtained was aged overnight for 12 hr. isolated by filtration, dried and calcined at 900° C. for 4 hrs.

Example 3: La—Sr—FeO$_3$

A 0.2M metal nitrate solution was prepared by dissolving Fe(NO3)3 (0.1 M), La(NO3)3 (0.07M) and Sr(NO3)3 (0.03 M) in distilled water, here Fe:La:Sr ratio was 1:(1-x):x.::1:0.7:0.3 solution was added to a 0.6M 100 ml citric acid solution slowly to get clear solution. Red gel was obtained by heating this solution in water bath at 80° c. for several hours. This gel was dried in oven at 120° c. for 5 hr in oven then temperature of oven was raised to 400° C. at rate of 1° c. and calcined 650° c. for 6 hrs.

Example 4: Zr—Mg Oxide

Hydrated Magnesia-zirconia oxide was obtained by co precipitation method. Magnesium nitrate 0.3 mol and zirconyl nitrate 0.1 mol were dissolved in 1.00 ml water to prepare mixed nitrate solution. This solution was then added to 500 ml water at room temperature at 25° C. with constant stirring. This solution was maintained at pH 9 by adding 14.7 molar NH$_3$ solution (16.4 ml). White precipitate thus obtained was aged overnight for 12 hr, isolated by filtration, dried and calcined at 900° C. for 4 hrs.

Example 5: Ce—Mg Oxide

Hydrated ceria-magnesia oxide was obtained by co precipitation method. Cerium nitrate 0.3 mol and Magnesium nitrate 0.1 mol were dissolved in 100 ml water to prepare mixed nitrate solution. This solution was then added to 500 ml water at room temperature at 25° C. with constant stirring. This solution was maintained at pH 9 by adding 14.7 molar NH$_3$ solution (9.2 ml). White precipitate thus obtained was aged overnight for 12 hr. isolated by filtration, dried and calcined at 900° C. for 4 hrs.

Example 6

Precursors for Ce$_{(1-x)}$M$_x$O$_2$ solid solutions were obtained by refluxing aqueous solution containing appropriate amount of metal nitrates and urea for 48 hrs. Total metal nitrate concentration in this solution was 0.4 M where as initial urea:nitrate ion ratio was 1.6:1. Solid precursor thus obtained was isolated by pressure filtration and washed thoroughly 1$^{st}$ with water and then with ethanol to remove any uncomplexed ions. Solid was dried in an oven at 100° C. for 8 hrs. ceria containing solid solution were then obtained by calcining this precursor at 500° C. for 4 hrs. Employing above described method various Ce$_{(1-x)}$M$_x$O$_2$ were prepared using Ce:Zr ratio ranging from 1:1, 2:1, 3:1 and 5:1.

Comparison of Activity for Catalyst Prepared by Both Urea and Co-Precipitation Method Out in 2 Liter CSTR Example 7

Methyl carbamate (MC) 125 g (1665 mmol) and methanol 265 g (8281.2 mmol) with 3.3 g of CeZrO (Ce:Zr::3:1) were charged to a 2000 ml reactor connected to a CO2 reservoir from gas inlet valve. The reservoir was fitted to reactor through constant pressure regulator which was set at 340 psi. A back pressure regulator was fitted to reactor at gas outlet valve. Back pressure regulator was set at 300 psi. The pressure difference of 40 psi was maintained between constant pressure regulator and back pressure regulator to ensure positive flow of CO2. This will help in stripping of CH$_3$OH along with NH$_3$ that is formed during reaction. The reactor was then pressurized with CO2 to 300 psi prior to heating from inlet valve. The inlet valve was closed at this point keeping outlet valve open. The contents were heated to 180° C. under very slow stirring condition. After attaining the temperature the inlet valve was opened. The methanol feeding was done at the rate of 7 ml/min. The reaction was continued for 6 h. During this period methanol along with $NH_3$ was expelled due to the set positive pressure of CO2. This methanol along with dissolved $NH_3$ was collected in a trap (cooled with ice and salt mixture) connected to BPR outlet. After completion of reaction the reactor was cooled to room temperature at 27° C. Reaction mixture from bomb as well as from trap was analyzed by Gas Chromatography. From GC analysis 68.1% conversion of methyl carbamate and 67.3% selectivity to DMC and 1.85% selectivity to MMC was observed in the reaction Example 8

Methyl carbamate (MC) 125 g (1665 mmol) and methanol 265 g (8281.2 mmol) with 3.3 g of CeZrO (Ce:Zr::3:1) were charged to a 2000 nil reactor connected to a $N_2$ reservoir from gas inlet valve. The reservoir was fitted to reactor through constant pressure regulator which was set at 340 psi. A hack pressure regulator was fitted to reactor at gas outlet valve. Back pressure regulator was set at 300 psi. The pressure difference of 40 psi was maintained between constant pressure regulator and back pressure regulator to ensure positive flow of CO2. This will help in stripping of $CH_3OH$ along with $NH_3$ that is formed during reaction. The reactor was then pressurized with N2 to 300 psi prior to heating from inlet valve. The inlet valve was closed at this point keeping outlet valve open. The contents were heated to 180° C. under very slow stirring condition. After attaining the temperature the inlet valve was opened. The methanol feeding was done at the rate of 7 ml/min. The reaction was continued for 6 h. During this period methanol along with $NH_3$ was expelled due to the set positive pressure of N2. This methanol along with dissolved $NH_3$ was collected in a trap (cooled with ice and salt mixture) connected to BPR outlet. After completion of reaction the reactor was cooled to room temperature at 30° C. Reaction mixture from bomb as well as from trap was analyzed by Gas Chromatography. From GC analysis 25.4% conversion of methyl carbamate and 44.8% selectivity to DMC and 0.33% selectivity to MMC was observed in the reaction Example 9

Methyl carbamate (MC) 12.5 g (1665 mmol) and methanol 265 g (8281.2 mmol) with 3.3 g of CeZrO (Ce:Zr::1:1) were charged to a 2000 ml reactor connected to a CO2 reservoir from gas inlet valve. The reservoir was fitted to reactor through constant pressure regulator which was set at 340 psi. A back pressure regulator was fitted to reactor at gas outlet valve. Back pressure regulator was set at 300 psi. The pressure difference of 40 psi was maintained between constant pressure regulator and back pressure regulator to ensure positive flow of CO2. This will help in stripping of $CH_3OH$ along with $NH_3$ that is formed during reaction. The reactor was then pressurized with CO2 to 300 psi prior to heating from inlet valve. The inlet valve was closed at this point keeping outlet valve open. The contents were heated to 180° C. under very slow stirring condition. After attaining the temperature the inlet valve was opened. The methanol feeding was done at the rate of 7 ml/min. The reaction was continued for 6 h. During this period methanol along with $NH_3$ was expelled due to the set positive pressure of CO2. This methanol along with dissolved $NH_3$ was collected in a trap (cooled with ice and salt mixture) connected to BPR outlet. After completion of reaction the reactor was cooled to room temperature at 25° C. Reaction mixture from bomb as well as from trap was analyzed by Gas Chromatography. From GC analysis 35.6% conversion of methyl carbamate and 47.4% selectivity to DMC and 1.22% selectivity to MMC was observed in the reaction Example 10

Methyl carbamate (MC) 125 g (1665 mmol) and methanol 265 g (8281.2 mmol) with 3.3 g of CeZrO (Ce:Zr::2:1) were charged to a 2000 ml reactor connected to a CO2 reservoir from gas inlet valve. The reservoir was fitted to reactor through constant pressure regulator which was set at 340 psi. A back pressure regulator was fitted to reactor at gas outlet valve. Back pressure regulator was set at 300 psi. The pressure difference of 40 psi was maintained between constant pressure regulator and back pressure regulator to ensure positive flow of CO2. This will help in stripping of $CH_3OH$ along with $NH_3$ that is formed during reaction. The reactor was then pressurized with CO2 to 300 psi prior to heating from inlet valve. The inlet valve was closed at this point keeping outlet valve open. The contents were heated to 180° C. under very slow stirring condition. After attaining the temperature the inlet valve was opened. The methanol feeding was done at the rate of 7 ml/min. The reaction was continued for 6 h. During this period methanol along with $NH_3$ was expelled due to the set positive pressure of CO2. This methanol along with dissolved $NH_3$ was collected in a trap (cooled with ice and salt mixture) connected to BPR outlet. After completion of reaction the reactor was cooled to room temperature at 26° C. Reaction mixture from bomb as well as from trap was analyzed by Gas Chromatography. From GC analysis 35.7% conversion of methyl carbamate and 28.9% selectivity to DMC and 1.89% selectivity to MMC was observed in the reaction.

Example 11

Methyl carbamate (MC) 125 g (1665 mmol) and methanol 265 g (8281.2 mmol) with 3.3 g of CeZrO (prepared by urea hydrolysis procedure, Ce:Zr::5:1) were charged to a 2000 ml reactor connected to a CO2 reservoir from gas inlet valve. The reservoir was fitted to reactor through constant pressure regulator which was set at 340 psi. A back pressure regulator was fitted to reactor at gas outlet valve. Back pressure regulator was set at 300 psi. The pressure difference of 40 psi was maintained between constant pressure regulator and back pressure regulator to ensure positive flow of CO2. This will help in stripping of $CH_3OH$ along with $NH_3$ that is formed during reaction. The reactor was then pressurized with CO2 to 300 psi prior to heating from inlet valve. The inlet valve was closed at this point keeping outlet valve open. The contents were heated to 180° C. under very slow stirring condition. After attaining the temperature the inlet valve was opened. The methanol feeding was done at the rate of 7 ml/min. The reaction was continued for 6 h. During this period methanol along with $NH_3$ was expelled due to the set positive pressure of CO2. This methanol along with dissolved $NH_3$ was collected in a trap (cooled with ice and salt mixture) connected to BPR outlet. After completion of reaction the reactor was cooled to room temperature at 25° C. Reaction mixture from booth as well as from trap was analyzed by Gas Chromatography. From GC analysis 52.2% conversion of methyl carbamate and 62.6% selectivity to DMC and 1.93% selectivity to MMC was observed in the reaction.

Example 12

Methyl carbamate (MC) 125 g (1665 mmol) and methanol 265 g (8281.2 mmol) with 4 g of CeZrO (prepared by urea hydrolysis procedure, Ce:Zr::3:1) were charged to a 2000 ml reactor connected to a CO2 reservoir from gas inlet valve. The reservoir was fitted to reactor through constant pressure regulator which was set at 340 psi. A back pressure regulator was fitted to reactor at gas outlet valve. Back pressure regulator was set at 300 psi. The pressure difference of 40 psi was maintained between constant pressure regulator and back pressure regulator to ensure positive flow of CO2. This will help in stripping of $CH_3OH$ along with $NH_3$ that is formed during reaction. The reactor was then pressurized with CO2 to 300 psi prior to heating from inlet valve. The inlet valve was closed at this point keeping outlet valve open. The contents were heated to 180° C. under very slow stirring condition. After attaining the temperature the inlet valve was opened. The methanol feeding was done at the rate of 7 ml/min. The reaction was continued for 6 h. During this period methanol along with $NH_3$ was expelled due to the set positive pressure of CO2. This methanol along with dissolved $NH_3$ was collected in a trap (cooled with ice and salt mixture) connected to BPR outlet. After completion of reaction the reactor was cooled to room temperature at 25° C. Reaction mixture from bomb as well as from trap was analyzed by Gas Chromatography. From GC analysis 70.7% conversion of methyl carbamate and 64.2% selectivity to DMC and 1.57% selectivity to MMC was observed in the reaction Example 13

Methyl carbamate (MC) 125 g (1665 mmol) and methanol 265 g (8281.2 mmol) with 3.3 g of CeZrO (prepared by urea hydrolysis procedure, Ce:Zr::3:1) were charged to a 2000 ml reactor connected to a CO2 reservoir from gas inlet valve. The reservoir was fitted to reactor through constant pressure regulator which was set at 340 psi. A back pressure regulator was fitted to reactor at gas outlet valve. Back pressure regulator was set at 300 psi. The pressure difference of 40 psi was maintained between constant pressure regulator and back pressure regulator to ensure positive flow of CO2. This will help in stripping of $CH_3OH$ along with $NH_3$ that is formed during reaction. The reactor was then pressurized with CO2 to 300 psi prior to heating from inlet valve. The inlet valve was closed at this point keeping outlet valve open. The contents were heated to 180° C. under very slow stirring condition. After attaining the temperature the inlet valve was opened. The methanol feeding was done at the rate of 7 ml/min. The reaction was continued for 6 h. During this period methanol along with $NH_3$ was expelled due to the set positive pressure of CO2. This methanol along with dissolved $NH_3$ was collected in a trap (cooled with ice and salt mixture) connected to BPR outlet. After completion of reaction the reactor was cooled to room temperature at 25° C. Reaction mixture from bomb as well as from trap was analyzed by Gas Chromatography. From GC analysis 68.1% conversion of methyl carbamate and 67.3% selectivity to DMC and 1.85% selectivity to MMC was observed in the reaction.

Example 14

Methyl carbamate (MC) 125 g (1665 mmol) and methanol 265 g (8281.2 mmol) with 3.3 g of CeZrO (prepared by urea hydrolysis procedure, Ce:Zr::3:1) were charged to a 2000 ml reactor connected to a CO2 reservoir from gas inlet valve. The reservoir was fitted to reactor through constant pressure regulator which was set at 340 psi. A back pressure regulator was fitted to reactor at gas outlet valve. Back pressure regulator was set at 300 psi. The pressure difference of 40 psi was maintained between constant pressure regulator and back pressure regulator to ensure positive flow of CO2. This will help in stripping of $CH_3OH$ along with $NH_3$ that is formed during reaction. The reactor was then pressurized with $CO_2$ to 300 psi prior to heating from inlet valve. The inlet valve was closed at this point keeping outlet valve open. The contents were heated to 190° C. under very slow stirring condition. After attaining the temperature the inlet valve was opened. The methanol feeding was done at the rate of 7 ml/min. The reaction was continued for 6 h. During this period methanol along with NFL was expelled due to the set positive pressure of CO2. This methanol along with dissolved $NH_3$ was collected in a trap (cooled with ice and salt mixture) connected to BPR outlet. After completion of reaction the reactor was cooled to room temperature at 25° C. Reaction mixture from bomb as well as from trap was analyzed by Gas Chromatography. From GC analysis 69% conversion of methyl carbamate and 63.7% selectivity to DMC and 2.25% selectivity to MMC was observed in the reaction.

Experiments Using Catalyst Prepared by Co-Precipitation Method Under Batch Mode

Example 15

Methyl carbamate (MC) 7.5 g (100 mmol) and methanol 65 g (2030 mmol) were charged to a 300 ml reactor with 1 g of CeZrO (Ce:Zr::3:1). The contents were heated to 190° C. with slow stirring. After attaining the temperature; stirring speed was increased to 1000 rpm and the time was noted as zero time. The reaction was continued for 8 hours. Ammonia formed during the reaction was removed using cooled high pressure condenser (condenser was cooled to 15° C.) fitted above the gas outlet valve of the reactor. Ammonia was removed at the interval of 1 hour during the course of the reaction. After 8 h reaction; the reactor was cooled to room temperature at 25° C. Reaction mixture was analyzed by Gas Chromatography. 44.7% conversion of MC was observed with 18.9% selectivity towards dimethyl carbonate (DMC).

Example 16

Methyl carbamate (MC) 7.5 g (100 mmol) and methanol 65 g (2030 mmol) were charged to a 300 ml reactor with 1 g of LaZrO (La:Zr::1:3). The contents were heated to 190° C. with slow stirring. After attaining the temperature; stirring speed was increased to 1000 rpm and the time was noted as zero time. The reaction was continued for 8 hours. Ammonia formed during the reaction was removed using cooled high pressure condenser (condenser was cooled to 15° C.) fitted above the gas outlet valve of the reactor. Ammonia was removed at the interval of 1 hour during the course of the reaction. After 8 h reaction; the reactor was cooled to morn temperature. Reaction mixture was analyzed by Gas Chromatography. 11.3% conversion of MC was observed with 10.9% selectivity towards dimethyl carbonate (DMC).

Example 17

Methyl carbamate (MC) 7.5 g (100 mmol) and methanol 65 g (2030 mmol) were charged to a 300 ml reactor with 1 g of LaFeSrO (Fe:La:Sr::1:0.7:0.3). The contents were heated to 190° C. with slow stirring. After attaining the temperature stirring speed was increased to 1.000 rpm and the time was noted as zero time. The reaction was continued for 8 hours. Ammonia formed during the reaction was removed using cooled high pressure condenser (condenser was cooled to 15° C.) fitted above the gas outlet valve of the reactor. Ammonia was removed at the interval of 1 hour during the course of the reaction. After 8 h reaction; the reactor was cooled to room temperature at 25° C. Reaction mixture was analyzed by Gas Chromatography. 53.7% conversion of MC was observed with 13.2% selectivity towards dimethyl carbonate (DMC).

Example 18

Methyl carbamate (MC) 125 g (1665 mmol) and methanol 265 g (8281.2 mmol) with 3.3 g of CeZrO (3:1::Ce:Zr prepared by urea hydrolysis) were charged to a 2000 ml reactor connected to a CO2 reservoir from gas inlet valve. The reservoir was fitted to reactor through constant pressure regulator which was set at 340 psi. A hack pressure regulator was fitted to reactor at gas outlet valve. Back pressure regulator was set at 300 psi. The pressure difference of 40 psi was maintained between constant pressure regulator and back pressure regulator to ensure positive flow of CO2. This will help in stripping of $CH_3OH$ along with $NH_3$ that is formed during reaction. The reactor was then pressurized with CO2 to 300 psi prior to heating from inlet valve. The inlet valve was closed at this point keeping outlet valve open. The contents were heated to 180° C. under very slow stirring condition. After attaining the temperature the inlet valve was opened. The methanol feeding was done at the rate of 7 ml/min. The reaction was continued for 6 h. During this period methanol along with $NH_3$ was expelled due to the set positive pressure of CO2 This methanol along with dissolved $NH_3$ was collected in a trap (cooled with ice and salt mixture) connected to BPR outlet. After completion of reaction the reactor was cooled to room temperature at 25° C. Reaction mixture from bomb as well as from trap was analyzed by Gas Chromatography. From GC analysis 68.1% conversion of methyl carbamate and 67.3% selectivity to DMC and 1.85% selectivity to MMC was observed in the reaction Example 19

Propyl carbamate (PC) 94.5 g (916.9 mmol) and propanol 275.5 g (4587 mmol) with 3 g of CeZrO (3:1::Ce:Zr prepared by urea hydrolysis) were charged to a 2000 ml reactor connected to a CO2 reservoir from gas inlet valve. The reservoir was fitted to reactor through constant pressure regulator which was set at 340 psi. A back pressure regulator was fitted to reactor at gas outlet valve. Back pressure regulator was set at 300 psi. The pressure difference of 40 psi was maintained between constant pressure regulator and back pressure regulator to ensure positive flow of CO2. This will help in stripping of $CH_3OH$ along with $NH_3$ that is formed during reaction. The reactor was then pressurized with CO2 to 300 psi prior to heating from inlet valve. The inlet valve was closed at this point keeping outlet valve open. The contents were heated to 180° C. under very slow stirring condition. After attaining the temperature the inlet valve was opened. The methanol feeding was done at the rate of 7 ml/min. The reaction was continued for 6 h. During this period methanol along with $NH_3$ was expelled due to the set positive pressure of CO2. This methanol along with dissolved $NH_3$ was collected in a trap (cooled with ice and salt mixture) connected to BPR outlet. After completion of reaction the reactor was cooled to room temperature at 25° C. Reaction mixture from bomb as well as from trap was analyzed by Gas Chromatography. From GC analysis 21.8% conversion of propyl carbamate and 52.7% selectivity to DPC was observed in the reaction.

Example 20

Ethyl carbamate (EC) 94.5 g (1060 mmol) and ethanol 245 g (5321 mmol) with 3 g of CeZrO (3:1::Ce:Zr prepared by urea hydrolysis) were charged to a 2000 ml reactor connected to a CO2 reservoir from gas inlet valve. The reservoir was fitted to reactor through constant pressure regulator which was set at 340 psi. A back pressure regulator was fitted to reactor at gas outlet valve. Back pressure regulator was set at 300 psi. The pressure difference of 40 psi was maintained between constant pressure regulator and back pressure regulator to ensure positive flow of CO2. This will help in stripping of $CH_3OH$ along with $NH_3$ that is formed during reaction. The reactor was then pressurized with CO2 to 300 psi prior to heating from inlet valve. The inlet valve was closed at this point keeping outlet valve open. The contents were heated to 180° C. under very slow stirring condition. After attaining the temperature the inlet valve was opened. The methanol feeding was done at the rate of 7 ml/min. The reaction was continued for 6 h. During this period methanol along with $NH_3$ was expelled due to the set positive pressure of CO2. This methanol along with dissolved $NH_3$ was collected in a trap (cooled with ice and salt mixture) connected to BPR outlet. After completion of reaction the reactor was cooled to room temperature at 27° C. Reaction mixture from bomb as well as from trap was analyzed by Gas Chromatography. From GC analysis 49.1% conversion of ethyl carbamate and 17% selectivity to DEC was observed in the reaction Example 21

Butyl carbamate (BC) 89.5 g (764.9 mmol) and butanol 283 g (3820 mmol) with 3 g of CeZrO (3:1::Ce:Zr, prepared by urea hydrolysis) were charged to a 2000 ml reactor connected to a CO2 reservoir from gas inlet valve. The reservoir was fitted to reactor through constant pressure regulator which was set at 340 psi. A back pressure regulator was fitted to reactor at gas outlet valve. Back pressure regulator was set at 300 psi. The pressure difference of 40 psi was maintained between constant pressure regulator and back pressure regulator to ensure positive flow of CO2. This will help in stripping of $CH_3OH$ along with $NH_3$ that is formed during reaction. The reactor was then pressurized with CO2 to 300 psi prior to heating from inlet valve. The inlet valve was closed at this point keeping outlet valve open. The contents were heated to 185° C. under very slow stirring condition. After attaining the temperature the inlet valve was opened. The methanol feeding was done at the rate of 7 ml/min. The reaction was continued for 6 h. During this period methanol along with $NH_3$ was expelled due to the set positive pressure of CO2. This methanol along with dissolved $NH_3$ was collected in a trap (cooled with ice and salt mixture) connected to BPR outlet. After completion of reaction the reactor was cooled to room temperature at 28° C. Reaction mixture from bomb as well as from trap was analyzed by Gas Chromatography. From GC analysis 20.7% conversion of butyl carbamate and 24.3% selectivity to DBC was observed in the reaction

ADVANTAGES OF THE INVENTION

1. With use of suitable preparation method and combination of rare earth/inner transition metals with transition metals or lanthanides it will be possible to tune acid base properties of mixed metal oxide catalysts to improve DMC selectivity,
2. Provides environmentally benign process for the synthesis of DMC
3. Catalyst provided is easy to separate.

The invention claimed is:

1. A process for the synthesis of dialkyl carbonates, using a catalyst of AB oxides supported on a support selected from carbon, neutral alumina or silica, the process comprising the steps of:
   a. charging alkyl carbamate and aliphatic alcohol (1:5) in a high pressure reactor, adding the catalyst and heating the reactor to 100-300° C. with stirring; and
   b. removing ammonia formed over the period of reaction and cooling the reaction to room temperature to obtain the desired alkyl carbonate;
   wherein the dialkyl carbonates are dimethyl carbonate (DMC), diethyl carbonate (DEC), dipropyl carbonate (DPC) or dibutyl carbonate (DBC); and
   wherein A and B are selected from rare earth, transition metals and alkaline earth metals and the AB oxide has an A:B ratio ranging from 0.5:10 to 10:0.5.

2. The process as claimed in claim 1, wherein the catalyst is a mixed metal oxide, said metal selected from rare earth/inner transition elements or transition metals.

3. The process as claimed in claim 2, wherein said catalyst is optionally a ternary mixed metal oxide having more than two elements used in combination in the molar ratio a:b:c, where element "a" is in a range of 0.1 to 1; element "b" is in a range of 0.1 to 1-x and element "c" is x, wherein x is in the range of 0.01 to 0.09, wherein said elements are selected from rare earth, transition metals and alkaline earth metals.

4. The process as claimed in claim 2, wherein the element is selected from Zr, Ce, Fe or La.

5. The process as claimed in claim 2, wherein metal oxide is CeZrO.

6. The process as claimed in claim 1, wherein the process is conducted with $CO_2$ or $N_2$ stripping.

7. The process as claimed in claim 1, wherein the process is conducted in batch or continuous mode in an autoclave, packed bed reactor or bubble column reactor.

8. The process as claimed in claim 1, wherein conversion of alkyl carbamate is >30% and selectivity is more than 30% to the corresponding alkyl carbonate.

9. A process for the synthesis of dialkyl carbonates using a catalyst, the process comprising the steps of:
   a. reacting an alkyl carbamate and an aliphatic alcohol in the presence of a catalyst in a pressurized reactor at 100-300° C. with stirring;
   b. removing ammonia formed over the period of reaction;
   c. cooling the reaction to room temperature; and
   d. isolating the synthesized dialkyl carbonate, the synthesized dialkyl carbonate selected from dimethyl carbonate (DMC), diethyl carbonate (DEC), dipropyl carbonate (DPC) and dibutyl carbonate (DBC);
   wherein the catalyst is an AB oxide having an A:B ratio ranging from 0.5:10 to 10:0.5, each of A and B being different elements selected from Mg, Sr, Zr, Ce, Fe and La.

10. The process of claim 9, wherein the catalyst is on a support, the support selected from carbon, neutral alumina or silica.

11. A process for the synthesis of dialkyl carbonates using a catalyst, the process comprising the steps of:
   a. reacting an alkyl carbamate and an aliphatic alcohol in the presence of the catalyst in a pressurized reactor at 100-300° C. with stirring;
   b. removing ammonia formed over the period of reaction;
   c. cooling the reaction to room temperature; and
   d. isolating the synthesized dialkyl carbonate, the synthesized dialkyl carbonate selected from dimethyl carbonate (DMC), diethyl carbonate (DEC), dipropyl carbonate (DPC) and dibutyl carbonate (DBC);
   wherein the catalyst is a mixed metal oxide having more than two elements used in combination in the molar ratio a:b:c, where element "a" is in a range of 0.1 to 1; element "b" is in a range of 0.1 to 1-x and element "c" is x, wherein x is in the range of 0.01 to 0.09, wherein elements a, b, and c of the mixed metal oxide are selected from rare earth, transition metals and alkaline earth metals.

12. The process of claim 11, wherein the catalyst is on a support, the support selected from carbon, neutral alumina or silica.

13. The process of claim 11, wherein each of a, b, and c of the mixed metal oxide are selected from Mg, Sr, Zr, Ce, Fe and La.

* * * * *